United States Patent [19]

Power et al.

[11] Patent Number: 5,030,572

[45] Date of Patent: Jul. 9, 1991

[54] SUNFLOWER REGENERATION FROM COTYLEDONS

[75] Inventors: Christopher J. Power, Boulder, Colo.; Ebrahim Firoozabady, Madison, Wis.

[73] Assignee: Lubrizol Genetics, Inc., Wickliffe, Ohio

[21] Appl. No.: 453,155

[22] Filed: Dec. 14, 1989

Related U.S. Application Data

[63] Continuation of Ser. No. 33,412, Apr. 1, 1987, abandoned.

[51] Int. Cl.$^5$ .............................................. C12N 5/00
[52] U.S. Cl. ............................ 435/240.5; 435/240.49; 435/240.54
[58] Field of Search ............ 435/240.49, 240.5, 240.54

[56] References Cited

U.S. PATENT DOCUMENTS 4,673,648  6/1987  Wilcox et al. .................. 435/240.54

OTHER PUBLICATIONS

Sadhu (1974) Indian J. Exp. Biol. 12:110–111.
Paterson and Everett (1985) Plant Science 42:125–132.
Rogers et al. (1974) In Vitro 9:463–467.
Georgieva-Todorova et al. (1980) Proc. of the 9th Int. Sunflower Conf., Torremolinas, Spain, vol. 1:122–128.
Bohorova et al. (1985) Z. Pflanzenzuchtg. 95:35–44.
Binding et al. (1981) Z. Pflanzenphysiol. 101:119–130.
Greco et al. (1984) Plant Science Lett. 36:73–77.
Trifi et al. (1981) Physiol. Feb. 19:99–102.
Paterson (1984) Amer. J. Bot. 71:925–931.
Chandler and Beard (1983) Crop Science 23:1004–1007.
Paterson (1985) Abstract Amer. J. Bot. 72:827.

Primary Examiner—Elizabeth C. Weimar
Assistant Examiner—David T. Fox
Attorney, Agent, or Firm—Greenlee and Associates

[57] ABSTRACT

A method for regeneration of sunflower plants via shoot induction from cotyledon explants prepared from non-germinated sunflower embryos is described. Several methods for preparing explants by dissection of mature and immature fully-formed embryos are provided. Explants are prepared to insure that substantially all of the induced shoots derive from single cotyledon cells. Appropriately prepared explants are cultured on a shoot induction medium containing a combination of BA and NAA. Induced shoots are rooted and the resulting plantlets are grown into mature sunflower plants. This regeneration method is efficient, rapid and employs a convenient explant source, sunflower seed. This regeneration method is particularly useful in combination with methods for introduction of foreign DNA into sunflower cells and tissue.

36 Claims, 1 Drawing Sheet

SUNFLOWER REGENERATION FROM COTYLEDONS

This application is a continuation of application Ser. No. 033,412, filed Apr. 1, 1987 now abandoned.

The present invention relates to a method for regeneration of sunflower plants from explants prepared from sunflower embryos and, more particularly, to regeneration via induction of shoots from cotyledonary tissue. Specifically, explants containing cotyledons or parts of cotyledons prepared from embryos are cultured on a shoot induction medium to produce shoots from cells at or near the cut surface of the cotyledonary tissue. Shoots are then rooted to produce plantlets which develop into whole sunflower plants. The present invention also relates to a shoot induction medium for regeneration from cotyledonary tissue and to sunflower plants and their progeny seed produced by the regeneration method.

BACKGROUND OF THE INVENTION

Sunflower is one of the four major oilseed crops in the world (see Carter (ed.) (1978) *Sunflower Science and Technology*, Agronomy Monograph 19, American society of Agronomy, Madison, Wisc.). Sunflower oil is used mainly as an edible oil and in food manufacturing. Sunflower seeds are also grown as a confectionery as well as for bird and animal feed. Significant effort has been expended in conventional breeding programs to obtain sunflower cultivars having improved agronomic characteristics, particularly those having improved oil content or quality. (see Fick (1978) in *Sunflower Science and Technology*, Agronomy Monograph 19, American Society of Agronomy, Madison, Wisc., pp. 279-370.) Efficient methods of sunflower regeneration are useful for facilitating breeding programs for improved cultivars by providing rapid multiplication of plants having desirable traits. The availability of a large number of regenerated plants increases the speed of selection and further breeding cycles. It is also of considerable interest to apply the methods of plant genetic engineering to develop improved sunflower cultivars. The application of these methods to sunflower improvements requires the development of methods for the efficient production of plants which have been transformed to contain foreign DNA. A number of methods are now available which allow the introduction of DNA into and selection of transformed plant cells or tissue. The regeneration of whole transformed plants from cells or tissue is often difficult or inefficient. For this reason regeneration methods that are suitable for use in combination with methods of transforming plant tissue are useful in the production of whole transformed plants.

The genus Helianthus comprises about 67 species, including the common sunflower, *Helianthus annuus* L. *Helianthus annuus* includes a number of cultivars or varieties including wild, weed and cultivated varieties (see Heiser (1978) in *Sunflower Science and Technology*, Agronomy Monograph 19, American Society of Agronomy, Madison, Wisc.).

The term regeneration, as used herein, relates to the vegetative or asexual formation of progeny plants from somatic cells of a parent plant. Regeneration can proceed by the induction of plant organs, particularly shoots (organogenesis) or by the induction of somatic embryos (embryogenesis) from tissues of the parent plant. Previously, shoots or embryos have typically been generated from dedifferentiated callus induced from explant tissue of the parent plant. Regeneration also refers to asexual propagation of shoots from already differentiated axillary buds in meristem, shoot tip or bud explants. This process is also called shoot multiplication or shoot proliferation. Organogenic shoots or proliferated shoots are rooted and grown into whole regenerated plants. Somatic embryos are cultured and either develop shoots which must be rooted or grow into whole plantlets with shoots and roots. Embryogenesis is distinct from embryo culture which involves the in vitro culture of zygotic embryos. Embryo culture has been used, in particular, to develop embryos resulting from interspecific crosses which often do not survive in vivo. Embryo culture provides a single plant from the cultured embryo, while embryogenesis can provide multiple embryos and plantlets from a single parent.

Several methods of sunflower regeneration have been reported. These methods include organogenesis and embryogenesis as well as shoot proliferation from meristematic tissue. A variety of explant sources have been used and a number of media variations have been employed.

Sadhu (1974) Indian J. Exp. Biol 12: 110-111 reported the differentiation of plantlets with roots and shoots from callus initiated from sunflower stem pith explants. A modified White's culture medium (White (1963) in *The Cultivation of Animal and Plant Cells*, Ronald Press Co, New York) (see Table 1 and Table 5) containing 1 ppm of the auxin, indole-3-acetic acid (IAA), was used. It was reported that neither 2,4-dichlorophenoxyacetic acid (2,4-D) nor kinetin supported regeneration in this system. The sunflower varieties used for this work were not described and no indication of the efficiency of the regeneration process was provided. Later reports (Paterson and Everett (1985) Plant Science 42:125-132; Cooley and Wilcox, EPO patent applications 017904 and 0171593 (filed July 9, 1985) indicate that this method is not applicable to many sunflower varieties.

Rogers et al. (1974) In Vitro 9:463 reported the establishment of callus cultures from sunflower stem explants. Explants from a single sunflower line were examined. Sunflower callus was subcultured for 7 months, then transferred to a differentiation medium containing the hormone combination: 2 mg/l IAA and 0.5 mg/l kinetin. It was reported that sunflower calli developed "tufts of hairs" at about 1 month and roots at about 3 months. Whole plants were, however, not formed from these structures.

Georgieva-Todorova et al. (1980) Proceedings of the Ninth International Sunflower Conference, Torremolinas, Spain, Vol. 1:122-128 and Bonorova et al. (1985) Z. Pflanzenzuchtg. 95: 35-44 described organogenesis of sunflower shoots from callus induced from a variety of explants, particularly pith parenchyma and stem apices. It was reported that "meristem-like" structures as well as shoots and roots were produced from cultured callus tissue, and that optimum organogenesis was obtained on MS medium (Murashige and Skoog (1962) Physiol. Plant. 15:473-497) containing 0.1 mg/l 1-naphthaleneacetic acid (NAA), 0.1 mg/l benzyl adenine (BA), 0.01 mg/l gibberellic acid (GA) and 40 mg/l adenine sulfate. However, only 1-3 shoots/explant were obtained on this medium; increases up to 3-8 shoots/explant were obtained by further addition of 800 mg/l each of L-glutamine and L-asparagine. The technique was applied to several Helianthus species and interspecific hybrids and the type of development observed was reported to be dependent on genotype as well as culture conditions.

Bohorova et al., 1985 also described attempts to regenerate sunflower via androgenesis, that is, via callus induction from anthers. It was reported that callus could be induced from anthers, however, shoot induction from such callus was unsuccessful. Direct shoot formation from anthers was reported in two cases (*H. divaricatus* and the interspecific hybrid from *H. annuus* x *H. decapetalus*) on a medium containing 5 mg/l zeatin. Shoots generated in this way could be used to induce callus from which more shoots could be generated.

Binding et al. (1981) Z. Pfanzenphysiol. 101: 119–130 described the regeneration of a variety of dicotyledonous plants from isolated protoplasts. Sunflower protoplasts were regenerated on V-KM agar which contained the hormones: 2.5 $\mu$M BA, 5 $\mu$M NAA and 0.5 $\mu$M 2,4-D or on B5 medium (Gamborg et al. (1968) Exp. Cell Res. 50:151–158) containing 15 $\mu$M BA. Whole sunflower plants were produced by rooting of regenerated shoot cuttings. The genotype of sunflower used and the efficiency of the regeneration were not reported.

Greco et al., (1984) Plant Science Lett. 36:73–77 reported the regeneration of sunflower plants from a variety of explants derived from seedlings. Seedlings having the first pair of non-cotyledonary leaflets were employed as the source of explants. Explants included hypocotyl segments, cotyledon parts, leaflet pieces and shoot apices. Explants were cultured on MS medium supplemented with BA and/or 2,4-D at a variety of concentrations. It was reported that cotyledon parts cultured in the presence of 2,4-D alone or in combination with BA in some cases developed callus (after about 1 month) that contained many "translucent nodules, " while cotyledon parts cultured on BA alone displayed different kinds of development which was dependent on BA concentration. Cotyledon parts cultured on 1.0 mg/l BA produced no callus, but after about 1 month, 21% of the explants produced shoots directly. It was reported that one such explant produced 26 shoots. Culture of cotyledon parts on 5.0 mg/l BA resulted in the production of callus which on reculture produced shoots. In contrast, culture of cotyledon parts on an intermediate level of BA (3.0 mg/l) induced numerous "green bulges" on the tissue surface and eventually abundant callus, but no shoots. No indication of shoot morphology was given and regeneration of whole plants from the explant induced shoots was not reported. Only one variety of sunflower ('Sannace') was employed in these experiments.

Paterson and Everett, 1985, and Australian Patent 39152/85, filed Feb. 26, 1985, reported a method for regeneration of sunflower plants from callus induced from seedling hypocotyl explants. The medium used for callus induction and regeneration was optimized using an inbred line of sunflower and contained: MS medium (salts and vitamins) with additions of 5 g/l KNO$_3$, 100 mg/l myo-inositol, 40 mg/l adenine sulfate and 500 mg/l casamino acids with hormones: 1 mg/l NAA, 1 mg/l BA and 0.1 mg/l gibberellic acid and 30 g/l sucrose as the carbohydrate source. The best regeneration frequency was about 9.8 shoots/hypocotyl segment. Both BA and NAA were required for successful regeneration and addition of 5 g/l KNO$_3$ (to make a total KNO$_3$ concentration of 6.9 g/l) greatly improved regeneration frequency. The best explants were taken from seedlings older than 5 days. Regenerability of the plants was reported to be genotype specific.

Cooley and Wilcox, EPO application 0170904, filed July 9, 1985, reported sunflower regeneration through organogenesis. The method involved culturing explants on a callus induction medium containing abacisic acid and BA, followed by subculturing callus on a shoot induction medium containing IAA and kinetin followed by subculturing shoots on a rotting medium. A related method of sunflower regeneration through embryogenesis was reported by Cooley and Wilcox EPO Application 0172377, filed July 9, 1985. This method involved culturing explants on a medium containing 2,4-D alone or in combination with abscisic acid in order to induce embryogenic callus, followed by subculturing the embryogenic callus on an embryo regeneration medium containing IAA alone or in combination with kinetin, followed by subculturing somatic embryos on a plantlet development medium. In another related method, Cooley and Wilcox EPO application 0171593, filed July 9, 1985, reported sunflower regeneration through embryogenesis and organogenesis. The multi-step method involved culturing explant tissue on a callus induction medium containing abscisic acid and 2,4-D, followed by subculturing the callus on a preconditioning medium containing BA or abscisic acid with BA, followed by subculturing the callus on a shoot formation medium containing IAA, followed by subculturing the shoots on a root induction medium. An optional callus maintenance step was also described after the initial callus induction step. In all three of these regeneration methods the preferred explant tissue was described as immature whole embryos collected at 3–7 days after pollination (embryos being less than 0.1 mm in diameter).

Trifi et al. (1981) Physiol. Veg. 19:99–102 and Paterson (1984) Amer. J. Bot. 71:925–931 reported shoot multiplication of sunflower from shoot apices and nodes of seedlings. The medium used by Trifi et al. was MS medium with additions of 3% sucrose, 0.5 $\mu$g/l NAA and 0.5 $\mu$g/l BA. The medium used by Paterson contained either BA or kinetin, specifically BA at concentrations between 0.1 and 1.0 mg/l and kinetin at a concentration of 1 mg/l. The efficiency of shoot multiplication also demonstrated genotype variation.

Chandler and Beard (1980) The Sunflower 6:45–47 and Crop Science (1983) 23:1004–1007 described an embryo culture system which was employed to produce interspecific sunflower hybrids. Immature embryos were excised (3 to 7 days after pollination) and cultured using a two step method: the first step, embryo enlargement, employing a medium containing low auxin levels and high sucrose concentration followed by a second embryo germination step employing a mineral salts basal medium containing low sucrose.

Paterson (1984) Amer. J. Bot. 71:925–931 reported shoot multiplication from whole or half shoot apices of *H. annuus* seedlings. The optimal culture medium employed as MS medium with 0.1–1.0 mg/l BA or kinetin. All inbred lines (100) tested were reported to show shoot multiplication at least one media containing 1 mg/l kinetin. A large portion (51 to 100) of inbreds tested were also reported to produce adventitious shoots on the leaves of the multiple shoots that had been induced from culture apices. In contrast, adventitious shoots could only rarely be induced by culture of seedling leaves.

The present invention provides a novel, efficient method of regenerating sunflower plants from the cotyledons of non-germinated embryos. Both mature and immature embryos can be used as explant sources, as long as the cotyledons are fully formed. The present method requires fewer steps and is more rapid than prior art methods since a separate callus induction step is not required. The present method employs a convenient explant source, sunflower seed. For many sunflower varieties mature seed can be used as the explant source, obviating the need to germinate and grow seedlings under sterile conditions as explant sources. The present method insures that substantially all of the induced shoots derive from single cotyledon cells rather than from proliferation of already differentiated multicellular apical buds. The present method of regeneration is generally useful for rapid multiplication and micropropagation of sunflowers and is particularly useful in combination with methods of transforming cells or tissue with foreign DNA and selecting transformed plants to obtain whole sunflower plants containing that foreign DNA.

SUMMARY OF THE INVENTION

It is a primary object of the present invention to provide a method of inducing shoots from explants containing cotyledon tissue of non-germinated embryos and a method for regenerating sunflower plants from such shoots. These methods are designed to be particularly useful for combination with methods of transforming sunflower tissue with exogenous DNA and selecting transformed plants. In general the regeneration method of the present invention includes the steps of inducing shoots from an appropriately prepared sunflower explant, culturing the explant on a shoot induction medium such that a cut surface containing cotyledon tissue is placed in contact with the medium and shoots are induced from cotyledon tissue, and rooting induced shoots to produce plantlets which are then grown in a suitable plant growth medium to produce mature sunflower plants. The method also optionally includes an induced shoot elongation step. The sunflower explants of the present invention are prepared from non-germinated embryos. Mature embryos or fully-formed immature embryos can be employed in the present invention. Explants of the present invention can be composed entirely of cotyledon tissue or can comprise cotyledon tissue on at least one cut surface.

Cotyledon explants are prepared by any of three cutting methods which comprise three embodiments of the present invention. The cutting methods are described with reference to FIG. 1 in which, for clarity, the pointed end (radicle end) of the embryo has been designated the bottom of the embryo. In the first cutting method, exemplified in FIG. 1a, and herein designated the single horizontal cut method, a single horizontal cut is made across the sunflower embryo parallel to and above the line of attachment of the cotyledons such that substantially all of the embryo meristem is below the cut, dividing the embryo into three portions: a bottom portion that contains the embryo axil and two excised cotyledons which are separated by the cut. Either of the cotyledon portions is employed as the cotyledon explant. Substantially all of the meristem is removed from the cotyledon explant when the cut is made so that any discernible primordial leaves present at the tip of the meristem remain attached to the embryo meristem. Alternatively, substantially all of the meristem is removed from the cotyledons when the cut is made at least about 0.5 mm above the line of cotyledon attachment. It is preferred that the horizontal cut be made from about 0.5 to 1 mm above the line of cotyledon attachment.

The second cutting method designated the multiple cut method, is a modification of the single horizontal cut method, in that the excised cotyledon portions prepared by the first method are further cut into multiple segments such that the segments are of a size suitable to support shoot induction. The method is exemplified as in FIG. 1b, the multiple horizontal cut, in which the excised cotyledons are cut into multiple segments with further horizontal cuts. Horizontal cut cotyledon segments that are at least about 1-1.5 mm in width have been found to be suitable to support shoot induction. The segmented excised cotyledon portions are then employed as cotyledon explants. As with the single horizontal cut method, the horizontal cut should be made such that substantially all of the embryo meristem is removed from the cotyledons. This can be done either by making the cut such that any discernible primordial leaves remain attached to the meristem or by making the cut at least about 0.5 mm above the line of cotyledon attachment. It is preferred that the horizontal cut be made from about 0.5 to 1 mm above the line of cotyledon attachment. It is preferred that the excised cotyledons be cut as diagrammed in FIG. 1b into 3-4 segments of approximately equal size with further horizontal cuts.

Figure 1A:
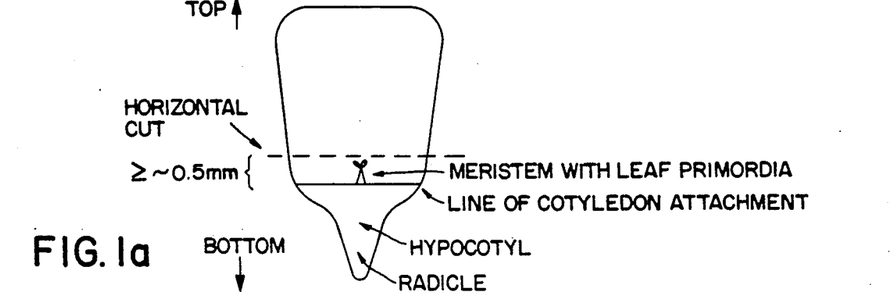
FIG. 1a details a single horizontal cut.
Figure 1B:
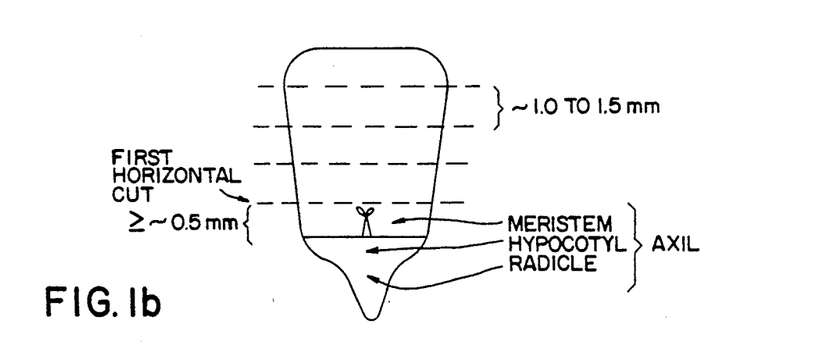
FIG. 1b details a multiple horizontal cut.
Figure 1C:
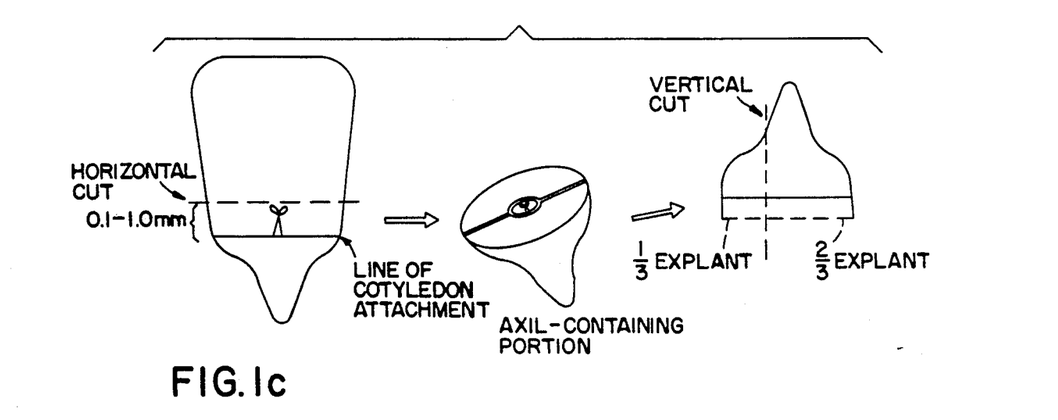

In the third cutting method, exemplified in FIG. 1c, and herein designated the $\frac{2}{3}$ cut method, a first horizontal cut is made across the sunflower embryo parallel to and above the line of cotyledon attachment such that most but not all of the cotyledon tissue is excised from the embryo axil. The cut should be made not more than about 1 mm above the line of cotyledon attachment. The horizontal cut divides the embryo into three portions: two excised cotyledons and a bottom axil-containing portion which contains the meristem, hypocotyl and radicle. The cut surface of the axil-containing portion comprises cotyledon tissue. In contrast to the other two cutting methods, the axil-containing portion is the explant source in the third cutting method. The axil-containing portion is cut a second time, along a line extending from one side of the radicle of the embryo to the surface of the first cut, thereby dividing the axil-containing portion into two segments that are about $\frac{1}{3}$ and $\frac{2}{3}$, respectively, the size of the whole portion. This second cut is made such that the meristem is not split. It is preferred that this cut be made vertically as exemplified in FIG. 1c. Both the $\frac{1}{3}$ and $\frac{2}{3}$ segments are employed as cotyledon explants. The position of the first horizontal cut in this method is important for obtaining cotyledon shoot induction from these explants. Making the first cut as described, above but not more than about 1 mm above the line of cotyledon attachment insures that the appropriate amount of cotyledon tissue remains at the surface of the axil-containing portion of the embryo. If the cut is made such that more cotyledon remains attached to this portion the zygotic embryo will develop and cotyledon shoot induction will be inhibited.

A shoot induction medium suitable for use in the regeneration method of the present invention contains a shoot-induction effective combination of an auxin and a cytokinin, a basal mineral salts medium suitable for sunflower tissue growth which must contain $KNO_3$ and a carbohydrate. In addition, shoot induction medium optionally comprises adenine sulfate, a plant growth effective vitamin solution and about 0.1 mg/l gibberellic acid. The preferred concentrations of $KNO_3$ are between about 1.9 to 10 g/l, with a range between about 6.9 to 10 g/l being more preferred and a concentration of 6.9 g/l being most preferred. It is preferred that the concentration of adenine sulfate in shoot induction medium be between about 10–100 mg/l, with a concentration of about 40 mg/l being most preferred.

The shoot induction effective combination of an auxin and a cytokinin is preferably benzyl adenine (BA) having a concentration between about 0.5 to 2.0 mg/l and 1-naphthaleneacetic acid (NAA) having a concentration between about 0.1 to 1.0 mg/l. The most preferred combination of hormones being 0.5 mg/l BA and 0.1 mg/l 1-NAA.

A shoot elongation step is optionally included in the method of the present invention when shoots induced on shoot induction medium are not long enough for effective rooting. Induced shoots having a length of at least about 1 cm and having from 4–8 leaves are generally suitable for rooting. However, shoots should be rooted before flower buds appear in order to maximize flower and seed development of resultant mature plants. Flower buds develop on shoots after about the 7th or 8th leaf has appeared, depending on culture condition and genotype. Induced shoots less than about 1 cm in length are transferred to shoot elongation medium to obtain shoots of appropriate length for rooting. Shoot elongation medium contains the same components as shoot induction medium, except that NAA and gibberellic acid are omitted and coconut water at concentrations from about 5%–20% (v/v) is optionally included.

In general, any rooting method that is suitable for use with shoots induced from sunflower explants can be employed in the regeneration method of the present invention. In particular, induced shoots can be rooted by short-term exposure of excised shoots to either indole-3-acetic acid or indole-3-butyric acid or equivalents at concentrations between about 10–100 mg/l, followed by culturing on a medium suitable for sunflower tissue growth which contains no plant hormones. It is preferred that treated shoots be cultured for rooting on conventional MS medium containing no plant hormones.

It is a further object of this invention to provide sunflower plants and their progeny seed which are produced by the regeneration method of the present invention.

BRIEF DESCRIPTION OF THE FIGURES

FIG. 1 provides schematic diagrams exemplifying methods for cutting mature and immature embryos to prepare cotyledon explants for shoot induction. FIG. 1c details a ⅔ cut. Broken lines represent the cut(s). The cuts are referenced to the line of cotyledon attachment (solid line) and the embryo axil (meristem, hypocotyl and radicle). For clarity, the radicle end of the embryo is designated the bottom of the embryo.

DETAILED DESCRIPTION OF THE INVENTION

In the sunflower regeneration method of the present invention, appropriately prepared cotyledon explants from either mature or fully-formed yet immature non-germinated embryos are first cultured on a shoot induction medium after which shoots of appropriate length and morphology are rooted and the resulting plantlets are then transferred to a planting medium for growth into mature sunflower plants.

The method of the present invention is particularly useful in combination with methods of transforming sunflower plants with foreign DNA in order to obtain transformed sunflower plants. A regeneration method that is suited for such an application should have several features Induced shoots should derive from single cells rather than from pre-formed buds in the meristem, since shoots induced from transformed single cells are more likely to result in uniformly transformed regenerated plants. It is also desirable that the time that the regenerating tissue is in a callus stage should be minimized in order to minimize somaclonal variation in regenerated plants. It is further desirable for such a regeneration method to be highly efficient to facilitate selection of regenerated transformed plants, particularly if DNA transformation is inefficient. Additional generally desirable features of the present method include the use of a convenient explant source, minimization of culture steps and manipulations and reduced time for plant regeneration from explants.

Explants employed in the present method are prepared by the embryo cutting methods diagrammed in FIG. 1 with reference to the anatomical features of the sunflower seed (see Knowles (1978) in *Sunflower Science and Technology*, Agronomy Monograph 19, American Society of Agronomy, Madison, Wisc., pp. 55–88), The fruit or achene of a sunflower comprises a seed or kernel enclosed in a pericarp or hull. The seed comprises an embryo covered with multiple layers of seed coat and a thin endosperm. The embryo comprises two cotyledons, a meristem, a hypocotyl and a radicle. The largest portion of the embryo is the cotyledons which are joined to the rest of the embryo along a line of attachment, as shown in FIG. 1. The meristematic tissue of the embryo is largely confined to the pointed end of the embryo below the line of attachment of the cotyledons. The meristem, hypocotyl and radicle of the embryo are also termed the axil of the embryo. The meristem extends above the line of cotyledon attachment, with a pair of primordial leaves often discernible at the upper tip of the meristem. Dependent somewhat on the size of the sunflower seed, the meristem can extend up to about 0.5 mm above the line of cotyledon attachment. For clarity, as shown in FIG. 1, the pointed end (radicle end) of the sunflower embryo is herein designated the bottom end of the embryo, and the cotyledon end of the embryo is designated the top end.

When whole fully-formed embryos are cultured on a medium containing nutrients, such as shoot induction medium (vide infra), they germinate and develop a single shoot with leaves and a root. If the embryo meristem, hypocotyl and radicle develop normally, i.e., germinate to form a plantlet, shoots cannot readily be induced from cotyledon tissue. Therefore, a method of preparing explants suitable for use in the present invention must either remove the embryo axil from the explant or disrupt development of the embryo axil.

In a first attempt, to prepare explants, sunflower embryos were cut longitudinally, splitting the embryo axil including the meristem to disrupt development of the embryo. Culture of such explants on shoot induction medium, however, led to undesirable proliferation of shoots from pre-formed buds in the meristem. Shoot induction from cotyledon tissue was not observed from these explants, so this cutting method and any other method of cutting the embryo that splits the meristem and results in shoot proliferation is not suitable for use in the present invention.

Cotyledon explants were prepared by three embryo cutting methods, which disrupt embryo development and avoid splitting the embryo meristem. Explants prepared by these culturing methods produce shoots from cotyledon tissue when cultured on shoot induction medium.

In a first embryo cutting method, a single horizontal cut is made across the embryo, parallel to and above the line of cotyledon attachment (see FIG. 1a) such that substantially all of the embryo meristem is below the cutting line. This cut detaches the embryo axil including substantially all of the meristem from the cotyledons, separates the two cotyledons and divides the embryo into three parts: two cotyledon portions and a bottom portion (as in FIG. 1a) which contains the embryo axil. The two excised cotyledons are then employed as explants. The horizontal cut should be made above the line of cotyledon attachment such that substantially all of the embryo meristem is removed from the excised cotyledon explant. The cut should be made such that any discernible primordial leaves at the tip of the meristem remain attached to the meristem. Alternatively, substantially all of the meristem should be removed by making the cut at least about 0.5 mm above the line of cotyledon attachment. Removing substantially all of the meristem from the excised cotyledon insures that most or all of the shoot induced on the explant will originate from single cotyledon cells rather than from pre-formed meristem buds. It is preferred that the horizontal cut be made as close to the line of cotyledon attachment as possible while still removing substantially all of the meristem from about 0.5 mm to 1.0 mm above the line of cotyledon attachment.

In a second procedure, the excised cotyledon explants prepared as in the single horizontal cut method are cut into multiple segments, as for example shown in FIG. 1b, in which the excised cotyledons are further cut with multiple horizontal cuts into segments of approximately the same size. It was found that if the excised cotyledon were cut into segments that were too small, shoot induction was not supported. Cutting the excised cotyledons into 3 or 4 segments approximately equal in size provided segments that supported shoot induction. These segments were about 1.0 to 1.5 mm thick. The horizontal cut which excises the cotyledons should be made as described in the single horizontal cut method (vide supra).

In a third cutting procedure, designated the ⅔ cut method, and exemplified in FIG. 1c, most but not all of the cotyledon tissue is excised from the embryo axil, again with a horizontal cut across the embryo, parallel to and above the line of cotyledon attachment. In contrast to the first and second cutting methods, the explant prepared by this method contains the embryo axil: meristem, hypocotyl and radicle (bottom portion, FIG. 1c). The horizontal cut is made above the line of cotyledon attachment dividing the embryo into three portions: two excised cotyledons and a portion that contains the embryo axil, such that cotyledon tissue remains at the cut surface of the portion that contains the embryo axil. The axil-containing portion of the embryo is then cut along a line extending from one side of the radicle to the surface of the horizontal cut, see FIG. 1c. This second cut divides the embryo portion into two segments: a larger segment, about ⅔ the size of the embryo portion which contains the axil, and a smaller segment, about ⅓ the size of the embryo portion. The second cut disrupts the normal development of the embryo, but does not split the meristem of the embryo. It is important to avoid splitting the meristem to prevent undesirable shoot proliferation from pre-formed buds. The second cut can be made vertically as shown in FIG. 1c. Both the ⅔ and ⅓ segments are employed as explants in this method of the present invention.

In the ⅔ cut method, the first horizontal cut is made as described herein such that a small amount of cotyledon tissue remains at the cut surface of the embryo portion that contains the axil. In positioning the horizontal cut, it is important to avoid retaining too much cotyledon tissue on the axil portion, since leaving more cotyledon tissue with the embryo axil will allow the embryo axil to develop and no cotyledonary shoots will be formed. Making the horizontal cut more that about 1 mm above the line of cotyledon attachment produces ⅔ explants which support embryo development. It is preferred that the cut be made about 0:1 to 1 mm above the line of cotyledon attachment and most preferably about 0.1 to 0.3 mm above that line.

As stated above, normal development of the embryo axil of the ⅔ segment explant is disrupted. In some cases, when ⅔ segments are cultured on shoot induction medium, some development of the hypocotyl and radicle occurs, including the appearance of enlarged leaves from the embryo meristem. This development stops at an early stage in properly prepared explants. In some cases, adventitious shoots developed on these explant leaves, producing shooty leaves. Shoots induced on leaves could be rooted and grown into mature plants; however, these shoots do not originate from the cotyldeon and may result from proliferation of pre-formed meristematic buds. The induction of shoots on explant leaves did not preclude cotyledon shoot formation; however, shooty leaf development appears to be inversely correlated with cotyledon shoot formation.

It was found that the cutting technique that was optimal for shoot induction was dependent on the genotype of sunflower to be regenerated and that not all cutting methods resulted in shoot induction with all genotypes. It was also found that the maturation stage of the embryos from which cotyledon explants were prepared affected the efficiency of shoot induction.

Sunflower embryos undergo distinct changes during maturation. In a first stage (about 1–3 weeks after fertilization), the entire embryo is transparent, semi-solid and very small. As the embryo increases in size, the outermost epidermal layers take on a beige color while the inner cotyledonary tissue remains transparent and semi-solid; this stage extends from about 3–4 weeks after pollination. In the third stage of immature embryos, the embryos reach maximum size, are beige-brown throughout and solid and the cotyledons are fully formed. This stage extends from about 4–8 weeks after pollination. When seeds are mature (about 5–10 weeks after pollination), the seeds cease drawing moisture from the parent, the embryos and pericarps become smaller, darker in color and more dense as the moisture content of the seed decreases. The maturation time for seeds can vary considerably with sunflower genotype and growing conditions, however the physical changes associated with the stages are conserved.

Only cotyledons from mature seeds or immature seeds in the third stage of development are useful in the present shoot induction and regeneration method. Cotyledons of fully-formed but immature embryos (third stage) generally produce shoots at higher efficiency than mature seed of the same cultivar. This result may be due to physiological differences between mature and immature seed, or simply due to tissue damage in the mature commercial seed that was employed. Mature seed from commercial sources may have been exposed to harsh or improper conditions during harvest or storage which have caused seed tissue damage and thereby affect the efficiency of shoot induction and regeneration. For this reason, mature seed of the same cultivar obtained from different sources and/or at different times can display considerably different regeneration efficiencies.

It was found that germinated embryos were not suitable sources of explants for the present invention. Germination is the process by which a zygotic embryo develops into a seedling. Zygotic embryos can be germinated in vitro by culturing on a nutrient medium. Germination is initiated by placing embryos on medium, after which imbibition or fluid uptake occurs and the embryo tissue displays swelling. After imbibition, visible hypocotyl and radicle development occurs. For sunflower cultivars used in the present work, no visible signs of embryo development were observed until more than 1-2 days after initiation of germination. At 1 day after initiation of germination, sunflower embryos generally displayed swelling without discernible embryo development. The effect of germination on induction of cotyledon shoots was examined. Whole embryos of inbred 5F were germinated in vitro on MS medium with and without 1.0 mg/l BA. Cotyledon explants were prepared from germinating embryos at 1, 3, and 6 days after initiation of germination, and the explants were cultured on shoot induction medium. Cotyledons taken from seeds 3 days or more after initiation of germination did not produce shoots on shoot induction medium. Cotyledon explants prepared 1 day after initiation of germination in the absence of BA displayed a shooting response similar to those prepared from non-germinated embryos, while those cultured on media containing BA displayed a poor shooting response. These results indicate that germinating embryos displaying discernible embryo development are not suitable for use in the present method. The term non-germinated embryo as used herein includes germinating embryos which display swelling but no visible signs of embryo development.

The ability of a particular plant cultivar to be regenerated appears to be genetically controlled, with certain cultivars having a high degree of regeneration potential compared to others. Conversely, certain cultivars will have little or no regeneration potential. Paterson, 1984, and Paterson and Everett, Australian patent 1985, have most recently examined regeneration potential in sunflower inbred lines. Their results suggest that the regeneration potential of a sunflower cultivar, at least from callus, is directly correlated to adventitious shoot formation on leaves and petioles from culture of shoot tips of that cultivar. Employing this correlation, they screened 100 inbred sunflower lines for regeneration potential and found that only a few lines (7) showed prolific adventitious shoot production, which they associated with high regeneration potential. In addition, they found that many sunflower lines tested (46) demonstrated no adventitious shoot production, presumably associated no less regeneration potential of these lines.

In the method of regeneration of the present invention, it was found that not all of the embryo cutting methods could be employed with all cultivars to obtain shoot induction. The 5F and 5MS inbred sunflower lines were regenerable from either mature or immature embryo explants prepared by all three cutting methods described herein. Mature 4M and 'Mammoth Russian' lines were regenerable from explants prepared by both the single horizontal cut and multiple horizontal cut method. For cultivar 'Mammoth Russian' considerable improvement in regeneration was observed when immature embryos were used as explants.

Of five hybrid lines employed in the present work, only hybrid 847 was readily regenerable from single horizontal cut explants. In the case of HA849 embryos, shoots were produced on leaves that developed from the meristem containing explant prepared by the ⅔ cut method, but no cotyledonary shoots appeared If regenerability is a heritable property, as has been suggested, (Paterson, 1984, for example), the regenerability of hybrid lines will be correlated with the regenerability of their inbred parent lines.

One of ordinary skill in the art employing the description provided herein can determine without undue experimentation which embryo cutting technique(s) can be employed in the present method for regeneration of a particular sunflower cultivar by preparing test explants for each of the cutting methods described herein (FIG. 1). These test explants are then cultured on a basic shoot induction medium which contains MS salts containing a total of 6.9 g/l KN03, 40 mg/l adenine sulfate, 100 mg/l myoinositol, 3% glucose, the plant hormone combination 0.5 mg/l BA and 0.1 mg/l NAA and 0:1 mg/l gibberellic acid. After about 21-28 days, cultured test explants are examined for production of cotyledonary shoots or shooty leaves, efficiency of shoot induction is determined and morphology of shoots is assessed. An embryo cutting method that is suitable for use in the present method with a particular sunflower cultivar produces explants from which shoots of normal or good morphology are induced on shoot induction medium. Test explants should be prepared from both mature and immature embryos of the cultivar. Once the appropriate embryo cutting method has been chosen, the shoot induction medium can be further optimized by assessing whether or not addition of 0.1 mg/l gibberellic acid or a vitamin solution leads to increased efficiency of shooting without adversely affecting shoot morphology. A regeneration method that proceeds through the induction of cotyledonary shoots rather than shoots from leaves derived from the meristem is preferred for combination with methods of transforming plants to contain foreign DNA.

In the present method shoot induction efficiency was assessed using two criteria: the percent of explants with shoots and the number of shoots/shooting explant. The percent of explants with shoots was noted after about 21 days on shoot induction medium. At the same time, the number of shoots/shooting explant was noted. Only discrete shoots having well-defined hairs, as seen through a dissecting microscope, were counted. It was found that the shooting frequency of similarly prepared and cultured explants could be highly variable. For this reason, the shooting frequency was assessed as an average number of shoots/shooting explant for a given cultivar and treatment. In all cases, the range of shoots/shooting explant was also noted.

In preparation for dissection and culturing of explants, sunflower embryos were sterilized (see Example 1) to prevent microbial overgrowth of explant cultures.

The sterilization conditions used were chosen to minimize microbial contamination but also to minimize embryo tissue damage due to sterilization treatments. Harsh sterilization treatment may lead to tissue damage which will adversely affect shoot induction and regeneration efficiency.

The term regeneration has sometimes been used in the art to describe the process of shoot induction, as in the usage "shoot regeneration". For clarity herein, when referring to the methods of the present invention the term shoot induction has been employed to describe induction of shoots on explants, while the term regeneration has been reserved to describe regeneration of whole plants via rooting of induced shoots The morphology of an induced shoot is known to be associated with the potential of that shoot to be rooted and grown into a whole plant. Shoot morphology that is normal or good, and associated with a better potential for successful rooting of shoots is characterized by shoots which are covered with shoot hairs and have dark green leaves with distinct veins. In contrast, poor or bad shoot morphology, associated with a decreased potential for successful rooting of shoots is characterized by shoots with few or no shoot hairs, which have glossy, succulent leaves with non-distinct or no veins The stems of shoots with poor morphology can either be translucent and light green or thick and succulent compared to normal stems. The morphology of shoots induced by the present method was found to be adversely affected by certain additions to shoot induction medium, including high hormone levels and, with some sunflower cultivars, gibberellic acid.

A shoot induction medium that is effective for sunflower cotyledon regeneration contains basal mineral salts which must include $KNO_3$, a carbohydrate and appropriate plant hormones. The medium must be maintained at a pH between about 4.0 and about 6.5, with a preferred range of about 5.0 to about 5.5. Additions of vitamins, amino acids and/or other nutrients can lead to improved efficiency or shooting frequency but are not essential for shoot induction.

A basal or minimal salts combination contains a mixture of mineral salts which provides inorganic components needed for plant tissue growth. Table 1 compares the compositions of several basal salts combinations that have been used in sunflower tissue culture. Paterson and Everett, 1985 have reported that MS (Murashige and Skoog, 1962), B5 (Gamborg, 1968) and also N6 (Chu (1975) Scientia Sinica 18:659–668) basal salts are suitable for growth of sunflower tissue in a sunflower regeneration method. MS salts were also employed by Georgieva-Todorova et at., 1980 and Bohorova et al., 1985 in shoot induction from sunflower callus. B5 salts was successfully employed in the sunflower regeneration methods of Binding et al., 1981 and Cooley and Wilcox (1985), as well as in sunflower embryo culture (Chandler and Beard, 1980 and 1983). Sadhu, 1974 reported generation of sunflower plantlets on a modified White's medium (see Table 1).

Paterson and Everett, 1985 have reported that additions of an extra 5.0 g/l of $KNO_3$ to MS salts medium considerably improved regeneration of shoots from sunflower hypocotyl explants. In the present work, it was found that $KNO_3$ was essential for shoot induction from sunflower cotyledon explants. Table 3 shows the variation in sunflower shoot induction efficiency as a function of $KNO_3$ concentration (0–10 g/l) added to the basal salts medium. In the experiments described in Table 3, various concentrations of $KNO_3$ were added to MS salts from $KNO_3$ had been omitted. No shoot induction was observed in the absence of $KNO_3$. Shoot induction was found to be better at $KNO_3$ concentrations between about 6.9 to about 10 g/l with about 6.9 g/l $KNO_3$ being optimal.

In the method of sunflower regeneration of the present invention any basal salts combination suitable for sunflower plant tissue culture can be employed as long as $KNO_3$ is also included. Shooting efficiency can, however, vary depending on the basal salts composition employed. MS basal salts (Table 1) is the preferred salts composition for the shoot induction medium of the present invention. The $KNO_3$ concentration of the basal medium can range from about 1.9 to about 10.0 g/l. The preferred range of $KNO_3$ concentration is from about 3.0 to about 10.0 g/l with a range from about 6.9 to about 10.0 g/l being more preferred, and about 6.9 g/l being most preferred.

Shoot induction from the sunflower cotyledon explants of the present invention requires a shoot induction effective combination of plant hormones which must include a cytokinin and an auxin. The preferred cytokinin is benzyl adenine (BA) and the preferred auxin is 1-naphthaleneacetic acid (NAA). The concentration range of cytokinin and auxin used was found to be important for regeneration efficiency and shoot morphology. The variation in shooting response of sunflower cotyledon explants to various levels of BA and NAA is presented in Table 2. The preferred range of BA concentration was from about 0.5. to about 2.0 mg/l, while the preferred range of NAA concentration was from about 0.1 to about 1.0 mg/l. Induced shoot morphology was found in general to be better at lower hormone concentrations, for example, the most preferred concentrations of BA and NAA were found to be about 0.5 mg/l and about 0.1 mg/l, respectively. It was also found, at least in combination with low levels of NAA, that BA concentration up to 2.0 mg/l could be employed in the present method (see Example 2). Shoot morphology was, however, poor at high BA levels. Several other cytokinins, including kinetin, zeatin and 2-isopentenyl adenine and auxins, including IAA, indole-3-butyric acid (IBA) and 2,4-D are known to the art. Those of ordinary skill in the art can determine without undue experimentation which cytokinins and auxins are suitable for use in the present regeneration method, and at what concentrations they should be employed For example, the inventors have found that IAA can be substituted for NAA in the shoot induction medium of the present method, although the shoot induction efficiency of cotyledons is somewhat lower when IAA is employed compared to NAA. It has also been found that 2,4-D is not suitable for use in the present method; the use of hormone combinations of BA and 2,4-D resulted in undesirable brown callus from which few or no shoots could be induced.

Either sucrose, glucose or equivalents alone or in combination can be used as the carbohydrate in the shoot induction medium of the present invention. Glucose is the preferred carbohydrate which results in improved shoot induction efficiency and shoots of better morphology. Carbohydrate levels ranging from about 1–3% (w/v) were preferred, with 3% (w/v) being most preferred.

A vitamin solution has typically been included in culture medium used for regeneration of sunflowers (see Paterson and Everett, 1985, for example). In the present method vitamin addition was not essential for shoot induction response from cotyledons. Table 4 shows the effect of addition of a vitamin solution, specifically a modified Nitsch's vitamin solution, the composition of which is provided in Table 5, on shooting response of cotyledon explants of several sunflower cultivar. In the experiment summarized in Table 4, adenine sulfate which is not a component of modified Nitsch's vitamin solution was included at 40 mg/l (vide infra). In two cases, addition of modified Nitsch's vitamins did not significantly affect shooting response; while in two other cases the addition of modified Nitsch's vitamins appeared to reduce shooting efficiency.

Table 5 compares the compositions of several vitamin solutions that nave been employed in sunflower regeneration methods. All of these vitamin solutions contain nicotinic acid (0:5-1.5 mg/l), thiamine HCl (0.1-10 mg/l), pyridoxine HCl (0.5-1.0 mg/l) and myo-inositol (100-500 mg/l). Vitamin solutions containing these components at these levels or equivalent are suitable for use in the present method Georgieva-Todorova et al., 1980 reported that addition of adenine sulfate at a level of 40 mg/l to regeneration medium significantly improved the regeneration response of sunflower explants. This was confirmed by Paterson and Everett, 1985. Table 6 shows the effect of variations in adenine sulfate levels on the shooting response of cotyledon explants. Adenine sulfate was not essential for shoot induction, however, addition of adenine sulfate at concentrations between about 10-100 mg/l did improve shooting efficiency. Table 6 also shows the variation in shooting response as a function of myo-inositol concentration. Again, layo-inositol was not essential for shoot induction, however addition of myo-inusitol at 100 or 500 mg/l improved shooting response Addition of 1000 mg/l of myo-inositol proved to slightly inhibit shooting response.

Several vitamin solutions that have been used in sunflower regeneration media include glycine and other amino acids which are added to media either as individual components or in the form of casein hydrolysate or casamino acids. Addition of either casamino acids or casein hydrolysate at levels of 500 or 1000 mg/l had no effect on shooting response in the present method. Bohorova et al., 1985 indicated that additions of the amino acids L-glutamine and L-asparagine could improve regeneration efficiency of sunflower explants. In the present work, these amino acids had no effect on shooting response when added at a level of 800 mg/l.

While no vitamins or amino acids are essential for shoot induction in the method of the present invention, it is preferred that adenine sulfate be included in the shoot induction medium at a level between about 10 and about 100 mg/l and that myo-inositol be included at a level between about 100 and about 500 mg/l. The most preferred concentrations of adenine sulfate and myo-inositol in shoot induction medium are about 40 mg/l and about 100 mg/l, respectively.

Bohorova et al., 1985 and Paterson and Everett, 1985 included gibberellic acid (0.01 mg/l and 0.1 mg/l, respectively) in sunflower regeneration media. The effect of addition of 0.1 mg/l of gibberellic acid on shooting response was variable. Shooting efficiency of certain sunflower cultivars, for example the inbred lines 5F and 5MS, was somewhat enhanced by addition of GA, while for other cultivars, for example inbred 4M and 'Mammoth Russian', GA addition decreased shooting efficiency. It was also found that addition of GA could in some cases adversely affect induced shoot morphology. The effect of GA acid addition should be assessed for each cultivar.

In summary, a basic shoot induction medium contains a suitable basal salts combination including KN03, most preferably 6.9 g/l $KNO_3$; adenine sulfate, most preferably 40 mg/l adenine sulfate; a carbohydrate, most preferably 3% glucose; and a suitable plant hormone combination, most preferably 0.5 mg/l BA and 0.1 mg/l NAA. In certain cases, shoot induction medium can be improved by addition of 0.1 mg/l gibberellic acid or by addition of a suitable vitamin solution.

After explants were cultured on shoot induction medium, induced shoots having a length of at least about 1 cm and having 4-8 leaves were cut from the shooting explant and rooted. Smaller shoots can be rooted by this method, but the survival of smaller rooted shoots after planting is significantly decreased so rooting of shoots less than about 1 cm in length is not effective in the present regeneration method. In some cases, particularly when a large number of shoots were induced on an explant, it was found to be necessary to transfer shoots that were too small to fresh nutrient medium, herein termed a shoot elongation medium, to obtain shoots of appropriate length for rooting. Elongated shoots were cut and rooted in the same manner as directly rooted shoots. Shoots should be cut for rooting before they produce any flower buds. Typically flower development occurs on shoots after about the 7th or 8th leaf has appeared, depending on culture conditions and sunflower genotype. Premature flowering of shoots in culture can lead to lower seed yield in mature plants. Shoot elongation medium has the same composition as shoot induction medium, except that NAA is omitted and coconut water (about 5 to 20% v/v) is optionally included. Gibberellic acid is also not included in shoot elongation medium.

Rooting was done by dipping shoots into solutions of IAA or IBA at concentrations from about 10-100 mg/l, followed by culture of treated shoots on MS medium to allow root development. MS medium consists of MS mineral salts (Table 1) and MS vitamins (Table 5), as described by Murashige and Skoog, 1962, and includes about 3% sucrose. Plant hormones and/or gibberellic acid are not included in this medium. The best rooting was obtained from shoots having normal, good morphology. Shoots having poor morphology were difficult to root. It was found that some improvement in root development was obtained by use of ½ strength MS medium.

Media were solidified using 0.8% agar (Taiyo agar) or 0.2% Gel-rite (Kelco Co., San Diego, Calif.). Gel-rite is an inert polysaccharide gelling agent comprising uronic acid rhamnose and glucose, which is described as less toxic to cells during culture. Gel-rite is the preferred solidifying agent, particularly for rooting of shoots. The use of lower concentrations of solidifying agent in the medium used for root development was generally preferred since rooted shoots would be more easily transferred from culture plates with less damage to young roots.

Plantlets were transferred to small containers of a peat-base soil mixture and kept in a vented plastic box in low light until new growth was evident (about 5-8 days). While mature regenerated plants were always somewhat stunted compared to the parent cultivar, they flowered and produced seed normally.

Other methods for rooting of shoots are known to the art and have been applied successfully to the rooting of sunflower shoots. For example, Paterson, 1984 reports that a grafting method originally developed by Haberman and Wallace (1958) Amer. J. Bot. 45:479–482 was successfully applied to the rooting of shoots generated from sunflower shoot tip explants.

The following examples are intended to further describe the present invention and are in no way intended to limit its scope.

EXAMPLE 1

Most mature seeds were obtained from commercial sources. Commercial hybrid lines used included Sigco 455, 468, 847, HA 849 and 7275 (dwarf line). Mature seed of proprietary female (5F and 5MS [male sterile]) and male (4M) parental inbred lines of Sigco 455 hybrid were obtained from Sigco Research Inc., Highway 75, Breckenridge, Minn. The commercial variety called 'Mammoth Russian' is essentially genetically identical to commercial varieties called 'Grey Stripe'. Herein the term 'Mammoth Russian' will be used for all such varieties. 'Mammoth Russian' seeds employed in these experiments were purchased from the American Seed Co., Newhaven, Mich., or as 'Grey Stripe' from the Feed and Seed Center, Jacksonville, Fla.

Immature seeds were obtained from open-pollinated, greenhouse grown plants. Immature seed heads were harvested when the pericarps were a dark color and the cotyledons were fully formed, but before moisture content of the seeds began to decrease (4–8 weeks after pollination; third stage of development). Immature seed heads can be stored at 1° C. in sealed containers for up to 6 weeks without deleterious effects on organogenic potential.

The pericarp or hull of each achene was removed. This can be conveniently done by cutting one edge of the hull with a scalpel and peeling away the hull by hand. Dehulled seeds were soaked for 1 minute in a 70% (v/v) 2-propanol/$H_2O$ mixture after which they were optionally rinsed twice in distilled water. Seeds were then sterilized for 20 minutes in a 20% bleach solution to which a surfactant was added. The addition of surfactant improves cleaning of the oily seeds. Optionally, a vacuum was applied co the sterilization solution to expel air bubbles. Harsher sterilization procedures should be avoided as they can lead to embryo tissue damage and decreased regeneration efficiency. After sterilization the seeds were rinsed several times with sterile distilled water. Seeds were then kept wet for 2-3 hours prior to dissection in order to ease removal of the seed coat. Shoot induction medium (without solidifying agent) was optionally used for the final rinse and to wet seeds prior to dissection. Care was taken to maintain sterile conditions during seed manipulation and dissection.

There are two coats on the dehulled sunflower seed: a papery, translucent seed coat and a thin, transparent endosperm layer within. Both of these layers were carefully peeled away using the tip of a scalpel blade. Embryos were then dissected by one of the techniques described below.

EXAMPLE 2: SHOOT INDUCTION MEDIUM

A basic shoot induction medium which contained MS salts containing 6.9 g/l $KNO_3$ (Table 1), modified Nitsch's vitamins (Table 5) with additions of 40 mg/l adenine sulfate and 3% sucrose was employed in order to optimize plant hormone levels for sunflower cotyledon shoot induction.

The regeneration or shoot induction response of cotyledon explants of mature embryos of the inbred line 5F to a 3×3 grid of BA (0, 0.5, 1.0 mg/l) and NAA (0, 0.1, 1.0 mg/l) levels was assessed (Table 2). Shoot induction efficiency was assessed by measuring both the percent of explants with shoots and the average number of shoots/explant with shoots after 21 days of culture. Shoot morphology was also noted. Sunflower shoots with normal, good morphology have dark green leaves with well-defined veins and the shoot is covered with shoot hairs. In contrast, shoots with poor or bad morphology have either light green sometimes translucent stems or succulent stems and have few or no shoot hairs. The leaves are glossy and succulent with few or no veins distinguishable. The leaves of shoots with poor morphology tend to be hard and narrower than leaves of shoots with good morphology. Normal or good shoot morphology generally correlates with increased rooting efficiency of shoots. The results of variations in BA and NAA levels are showed in Table 2. In this experiment cotyledon explants were prepared by either the ⅔ cut method or the multiple horizontal cut method as in FIGS. 1c and 1b, respectively (vide infra).

As shown in Table 2, no shooting was observed in the absence of BA or in the absence of NAA. The efficiency of the shooting response did not vary strongly over the range of combinations of NAA and BA used, however, shoot morphology was found to be significantly better at lower hormone concentrations.

A second experiment assessed shooting response of several sunflower cultivars to plant hormone combinations in which BA levels were varied (0.5, 1.0 and 2.0 mg/l) while the NAA concentration was held constant at 0.1 mg/l. Shooting was observed at all levels of BA used but shooting efficiency did not increase with increased BA. Shoot morphology again was found to be best at the lowest BA level.

The effect of variations of several medium components on shoot induction response of 5F cotyledon explants was assessed. Explants prepared by the ⅔ cut or multiple horizontal cut methods were cultured on shoot induction media in which the concentrations of $KNO_3$ (0–10.0 g/l), adenine sulfate (0–100 mg/l) and myo-inositol (0–1000 mg/l) were varied. The effect of varying the carbohydrate concentration and substituting glucose for sucrose was also examined. In each case, the basic medium noted above was employed except that the particular medium component being assessed was omitted. For example, when the concentration of $KNO_3$ was varied, the $KNO_3$ normally included in the basal salts was omitted. The effect of varying $KNO_3$ and adenine sulfate or myo-inositol levels are shown in Tables 2 and 6, respectively No shoot induction was observed on media containing no $KNO_3$. Shoot induction was observed on media containing levels of $KNO_3$ ranging from about 1.9 to 10 g/l, and shoot induction was better at $KNO_3$ levels of 6.9 to 10 g/l and best at 6.9 g/l $KNO_3$.

Neither adenine sulfate nor myo-inositol was essential for shoot induction. Addition of adenine sulfate at levels between 10–100 mg/l was beneficial for shoot induction. Addition of myo-inositol at levels of 100 or 500 mg/l improved the shooting response, while higher levels (1000 mg/l) slightly inhibited the shooting response.

It was found that sucrose or glucose alone or in combination could be used as the carbohydrate source in this method. The use of glucose (3% w/v) instead of, or in combination with sucrose, produced a visible difference in shoot morphology. In some cases, shoots induced on glucose containing media had denser longer shoot hairs than those grown on a medium containing only sucrose.

In related experiments, it was found that additions of casamino acid (500 or 1000 mg/l), casein hydrolysate (500 or 1000 mg/l), l-asparagine (800 mg/l) or l-glutamine (800 mg/l) had no visible effect on shoot induction efficiency or shoot morphology.

As described above, modified Nitsch's vitamins (see Table 5) were included in the basic medium used co assess medium variables. In a separate experiment, summarized in Table 4, the effect of addition of modified Nitsch's vitamin solution on shoot induction was assessed. It was found that in the present method vitamin addition was not essential to shoot induction and in fact for shoot induction from some cultivars addition of modified Nitsch's vitamins appeared to decrease the shooting response. It should be noted that in this experiment, adenine sulfate was always included at 40 mg/l.

Finally, the effect of addition of gibberellic acid (GA) as suggested by Bohorova et al., 1985 and Paterson and Everett, 1985, was assessed with cotyledon explants prepared from several sunflower cultivars. The effect of GA addition (at 0.1 mg/l) was variable: for some cultivars shooting efficiency was somewhat enhanced, while for other cultivars shooting efficiency was decreased. In some cases, it was found that although shoot induction was enhanced, GA addition adversely affected shoot morphology.

EXAMPLE 3: SINGLE HORIZONTAL CUT METHOD WITH CULTIVAR 5MS (INBRED LINE)

Mature seeds of the sunflower female inbred line 5MS were dehulled and sterilized as described in Example 1. After peeling away the seed coats, the embryos were dissected as shown in FIG. 1a. A single horizontal cut was made across the body of the embryo 0.5 to 1.0 mm above the attachment line of the cotyledons. Two excised cotyledon portions resulted from dissection of each embryo. The excised cotyledons were then placed on solidified shoot induction medium. Medium was dispensed into petri plates (100×25 mm, 30 ml/dish) and 5 cotyledons were placed on each plate. The cut ends of the cotyledons were pushed into the medium. This was found to be important for shoot induction. Each dish was sealed with tape. Light was supplied by cool white fluorescent bulbs using an 18 hr photoperiod. No initial dark period was provided. Plates were kept at 21°-24° C. Shoots began to appear after about 12-15 days. The number of shoots per cotyledon and the percent of cotyledons with shoots were noted after 25-30 days; only discrete shoots with well-defined hairs (as seen through a dissecting microscope) were counted.

Highest shooting efficiency was observed with a shoot induction medium that contained MS salts with 6.9 g/l KNO$_3$, modified Nitsch's vitamins, 40 mg/l adenine sulfate, 3% glucose, 0.1 mg/l gibberellic acid, 0.5 mg/l BA and 0.1 mg/l NAA and optionally contained modified Nitsch's vitamins. Gel-rite 0.2% (Kelco, San Diego, California) was employed to solidify the medium. Up to about 95% of the cotyledon explants induced shoots with an average of 26 shoots/shooting cotyledon. Results from different experiments were highly variable, possibly due to the quality of mature seed employed; variation of about 15% were observed in the percent of cotyledons with shoots and variations of about 20% were observed in the average number of shoots/shooting cotyledon.

Small induced shoots about 2-3 mm long with 1 or 2 pairs of leaves were transferred to shoot elongation medium. Shoot elongation medium had the same composition as shoot induction medium except that NAA was omitted and 15% (v/v) coconut milk was added.

Elongated shoots (greater than or equal to about 1 cm in length) having up to 7-8 leaves were rooted by dipping the base of cut shoots into 100 mg/l of IAA or IBA followed by culturing on conventional MS medium (MS salts and vitamins) containing no plant hormones. Improved rooting was observed when ½ strength MS medium was employed. The use of 0.2% Gelrite as the solidifying agent was found to be better for root development than the use of agar. Treated shoots were cultured for 7-14 days to allow root development after which plantlets were planted in a soil/peat based planting mixture to allow development into mature plants with seed.

EXAMPLE 4: SINGLE HORIZONTAL CUT METHOD: VARIETY 'MAMMOTH RUSSIAN'

Commercial mature seed of the variety 'Mammoth Russian' was dehulled and sterilized as described in Example 1. After peeling away the seed coats, the embryos were dissected as described in Example 3 and shown in FIG. 1a. The excised cotyledons, two per embryo, were then placed on shoot induction medium and cultured as above.

The best shoot induction response for mature 'Mammoth Russian' single horizontal cut explants was observed with a shoot induction medium containing: MS salts +6.9 g/l KNO$_3$, modified Nitsch's vitamins, 40 mg/l adenine sulfate and 3% sucrose (solidified with 0.2% Gel-rite). Addition of 0.1 mg/l GA was found to decrease shooting efficiency. Up to about 40% (± about 15%) of the cotyledon explants induced shoots with an average number of 10.5±10% shoots/shooting cotyledons.

Shoots were elongated and rooted as described in Example 3. Whole regenerated plants with seed were obtained after growth of rooted shoots in a peat/soil growth mixture.

EXAMPLE 5: MULTIPLE HORIZONTAL CUT METHOD: MATURE SEED INBRED LINE 5F

Mature seeds of the female inbred line 5F were dehulled and sterilized as described in Example 1. After peeling away the seed coats, the embryos were dissected as shown in FIG. 1b. First a horizontal cut was made across the body of the embryo parallel to and above the line of cotyledon attachment. The cut was made such that any primordial leaves at the tip of the meristem remained attached to the meristem. The cut was made between about 0.1 to 0.3 mm above the line of cotyledon attachment. The resultant excised cotyledons were then sliced, with horizontal cuts parallel to the first cut, into several segments. The best results were obtained by cutting these cotyledons into 3-4 segments, each about 1.0 to 1.5 mm thick. Six or eight explant pieces of cotyledon were obtained by this dissection method.

Cotyledon explants were placed on shoot induction medium. Medium was dispensed into petri plates (30 ml/plate) and the six or eight explant pieces were placed on a single plate such that the cut surface(s) of the explants were placed in contact with the medium. Light was provided by cool white fluorescent bulbs using an 18 hour photoperiod. No initial dark period was provided. Plates were kept at 21°-24° C. Shoots began to appear at 8-10 days at or near one cut surface of each segment. The number of shoots/embryo and the percent embryos that had shoots were noted at 20-21 days; only discrete shoots with well-defined hairs were counted. Highest shoot induction efficiency was obtained on a shoot induction medium that contained: MS salts +6.9 g/l $KNO_3$, modified Nitsch's vitamins (Table 5) 40 mg/l adenine sulfate, 3% glucose, containing 0.5 mg/l BA and 0.1 mg/l Shoot induction medium was solidified using 0.8% agar (Taiyo agar). Eighty percent of the explants developed shoots with an average number of shoots/shooting explant of 94 (standard deviation of 45.7).

Induced shoots having a length of about 1 cm or greater having 6 to 8 leaves were rooted directly. Smaller shoots were subcultured (7-14 days) on a shoot elongation medium as described above except that 5-20% coconut milk was added and NAA was omitted, until they reached a length of between about 1-3 cm. Shoots should be rooted before any flower bud forms. Typically flower buds developed after the 7 or 8 leaves have appeared Initially, shoots were dipped in 100 mg/l IAA or IBA and cultured on conventional MS medium containing no plant hormones until roots developed (about 7 days). It was later found that concentrations of IAA or IBA ranging from about 10-100 mg/l could be employed with no significant difference in rooting efficiency. Plantlets were grown in a soil/peat based plant mixture to allow growth into mature plants.

EXAMPLE 6: MULTIPLE HORIZONTAL CUT METHOD: 'MAMMOTH RUSSIAN'

Mature seeds of the variety 'Mammoth Russian' purchased from the American Seed Co. (Newhaven, Mich.) were prepared as described in Example 1 and cut by the method of Example 5. These explants were cultured on a shoot induction medium containing MS salts including 6.9 mg/l $KNO_3$, 40 mg/l adenine sulfate, 100 mg/l myo-inositol, 500 mg/l casamino acids, 0:5 mg/l BA, 0.1 mg/l NAA and 3% sucrose. No shoots were induced on these explants. Additions of higher levels of BA (up to 2.0 mg/l) to the induction medium did not cause induced shoots.

Explants were then prepared from immature seed. Immature seed heads of the variety 'Mammoth Russian' were obtained as described in Example 1 after planting mature commercial seed. Immature seeds were dehulled and sterilized as described in Example 1 and explants prepared as in Example 5. These explants of immature seed were cultured on the same shoot induction medium as mature seeds and shoot induction was observed. The highest efficiency of shoot induction was, however, observed using a shoot induction medium containing MS salts containing 6:9 g/l $KNO_3$, modified Nitsch's; vitamins, 40 mg/l adenine sulfate, 3% glucose, 0.5 mg/l BA and 0.1 mg/l NAA. Eighty percent of the explants developed shoots with an average number of shoots/shooting explant of 18.3. Induced shoots were elongated when necessary, rooted and planted as described in Example 5.

In a separate experiment, employing mature seeds of variety 'Mammoth Russian', purchased as 'Grey Stripe' from the Feed and Seed Center, Jacksonville, Fla., explants were prepared as in Example 1 and cut as in Example 5. In this experiment, explants were cultured on shoot induction medium containing MS salts with 6.9 g/l $KNO_3$, 40 mg/l adenine sulfate, 100 mg/l myo-inositol, 0.5 mg/l BA, 0.1 mg/l NAA and 0.1 mg/l gibberellic acid. In contrast to the previous experiment with mature seed described above, approximately 10% of these explants induced shoots with an average number of about 10-20 shoots per cotyledon.

EXAMPLE 7: ⅔ CUT METHOD: MATURE SEED INBRED LINE 5F

Mature seed of inbred line 5F was dehulled and sterilized as described in Example 1. After peeling the seed coats, the embryos were dissected as shown in FIG. 1c. A first horizontal cut was made across the body of the embryo, parallel to the line of cotyledon attachment and about 0.1 to 0:3 mm above this line. This cut detached much of the cotyledonary tissue from the meristem, hypocotyl and radicle of the embryo, leaving some cotyledon tissue attached to the meristem. The embryo portion containing the meristem was then cut along a line extending from one side of the radicle to the surface of the first cut, as shown in FIG. 1c. This cut divided that portion into 2 segments of ⅓ and ⅔ the size of the whole portion. The larger ⅔ segment, or ⅔ explant, contained the whole meristem of the embryo including the hypocotyl and radicle and a small portion of the cotyledon. The ⅓ explant was mostly cotyledon tissue. Both explants were cultured as described in Example 5, placing 3 explant pairs/30 ml medium.

The highest efficiency of shoot induction was observed using a shoot induction medium containing MS salts including 6.9 g/l $KNO_3$, modified Nitsch's vitamins, 40 mg/l adenine sulfate, 100 mg/l myo-inositol 3% glucose, 0.5, mg/l BA and 0.1 mg/l NAA. Fifty percent of the explants developed shoots with an average number of shoots/explant of 33.4 (standard deviation =21.1). Shoots were elongated, if necessary, rooted, and planted as described in Example 5.

EXAMPLE 8: ⅔ CUT METHOD: HYBRID LINES

Mature seeds of commercially available Sigco hybrids 455, 468, HA849 and the dwarf line 7275 were dehulled and sterilized as described in Example 1. The embryos were then dissected by the ⅔ cut method as described in Example 7. These explants were then cultured on a shoot induction medium containing MS salts with 6.9 g/l $KNO_3$, modified Nitsch's vitamins, 40 mg/l adenine sulfate, 100 mg/l myo-inositol 3% sucrose, 0.5 mg/l BA and 0.1 mg/l NAA. The medium was solidified with 0.8% agar. On culturing, hybrid HA849 explants produced enlarged leaves from the main meristem (⅔ segment) which developed clusters of adventitious shoots. This kind of development is herein designated shooty leaves. None of the other ⅔ cut explants of mature hybrid embryos developed shooty leaves, and none developed cotyledonary shoots. The adventitious shoots formed on leaves were rooted using the methods described in Example 5 and whole regenerated plants obtained.

Immature FI seed of the hybrids was obtained, as in Example 1, from open-pollinated, greenhouse grown plants. It should be noted that the FI hybrid seed is not necessarily genetically identical to the hybrid from which seed was obtained.

When ⅔ cut explants of immature embryos of the FI hybrid seed obtained from 455, 468, HA849 and 7275 were cultured on the shoot induction medium as above, shooty leaves were produced from 455, 7275 as well as 849. In addition, 455 and 7275 explants produced shoots at low frequency (about 1–5%) along the cut surface of the explant from cotyledonary tissue. Shoots from cotyledons or from leaves were rooted, and planted as described in Example 5.

Similar shooty leaves were produced on culture of inbred 4M ⅔ cut explants. In contrast, no shooty leaves were produced on culture of inbred 5F or 5MS ⅔ cut explants.

Those skilled in the art will appreciate that the invention described herein and the methods of preparing and culturing explants, plant tissue culture and sunflower cultivation described herein are susceptible to variations and modification other than as specifically described. It is to be understood that the invention includes all such variations and modification which fall within its spirit and scope.

TABLE 1

Composition and comparison of several basal salts media used in sunflower tissue culture

| Component | Concentration (mg/l) | | | | |
|---|---|---|---|---|---|
| | MS[1] | B5[2] | WH[3] | mod-WH[4] | N6[5] |
| $MgSO_4\ 7H_2O$ | 370 | 250 | 737 | 72 | 185 |
| $CaCl_2\ 2H_2O$ | 440 | 150 | — | — | 166 |
| $NH_4NO_3$ | 1650 | — | — | 400 | — |
| $KNO_3$ | 1900 | 2500 | 80 | 80 | 2830 |
| $KH_2PO_4$ | 170 | — | — | — | 400 |
| $(NH_4)_2SO_4$ | — | 134 | — | — | 463 |
| $NaH_2PO_4\ H_2O$ | — | 150 | 19 | — | — |
| $Ca(NO_3)_2\ 4H_2O$ | — | — | 288 | 144 | — |
| $KCl$ | — | — | 65 | 65 | — |
| $Na_2SO_4$ | — | — | 200 | — | — |
| $MnSO_4\ 4H_2O$ | 22.3 | — | 6.65 | — | 4.4 |
| $MnSO_4\ H_2O$ | — | 10 | — | 6.5 | — |
| $ZnSO_4\ 7H_2O$ | 8.6 | 2.0 | 2.67 | 2.7 | 1.5 |
| $CuSO_4\ 5H_2O$ | 0.025 | 0.025 | 0.001 | — | — |
| $CoCl_2\ 6H_2O$ | 0.025 | 0.025 | — | — | — |
| $KI$ | 0.83 | 0.75 | 0.75 | — | 0.8 |
| $H_3BO_3$ | 6.3 | 3.0 | 1.5 | 1.6 | 1.6 |
| $Na_2MoO_4\ 2H_2O$ | 0.25 | 0.25 | — | — | — |
| $MoO_3$ | — | — | 0.0001 | — | — |
| $FeSO_4\ 7H_2O$ | 27.85 | 27.85 | — | — | 27.85 |
| $Fe_2(SO_4)_3$ | — | — | 2.5 | — | — |
| $Na_2EDTA\ 2H_2O$[6] | 37.3 | 37.3 | — | 25 | 37.3 |

[1]Murashige and Skoog (1962) Physiol. Planta. 15:473–497.
[2]Gamborg et al. (1968) Exp. Cell Res. 50:151–158.
[3]Originally in White (1963) Cultivation of Animal and Plant Cells, 2nd ed., Ronald Press, New York, reevaluated and summarized in Evans et al. (1983) Handbook of Plant Cell Culture. Volume 1, Macmillan Pub. Co., New York
[4]Modified White's; Sadhu (1974) Indian J. Exp. Biol. 12:110–111
[5]Chu et al. (1975) Scientia Sinica 28:659–668
[6]EDTA = Ethylenediaminetetraacetate

TABLE 2

Shoot Induction response of sunflower inbred line 5F (mature embryos) to variations in hormone (NAA and BA) concentration.[1,2]

| BA (mg/l) | NAA (mg/l) | % Embryos with shoots | Shooting Response $x \pm S.E.$[3] | Range | Morphology |
|---|---|---|---|---|---|
| 0 | 0 | 0 | — | — | — |
| | 0.1 | 0 | — | — | — |
| | 1.0 | 0 | — | — | — |
| 0.5 | 0 | 0 | — | — | — |
| | 0.1 | 50% | 15.4 ± 3.5 | 1–43 | good |
| | 1.0 | 53% | 11.4 ± 2.0 | 1–32 | poor |
| 1.0 | 0 | 0 | — | — | — |
| | 0.1 | 40% | 14.8. ± 2.7 | 5–36 | fair |
| | 1.0 | 50% | 23.4. ± 3.7 | 4–43 | poor |

[1]NAA = 1-napthaleneacetic acid; BA = Benzyladenine.
[2]Both 2/3 and multiple horizontal cutting methods were employed. Shoot induction medium employed contained: MS basal salts with 6.9 g/l $KNO_3$, modified Nitsch's vitamins, 40 mg/l adenine sulfate, 3% sucrose.
[3]x = Average number of shoots/embryo with shoots and S.E. = Standard Error; N = 20.

TABLE 3

Shoot Induction response of sunflower inbred line 5F to various levels of $KNO_3$.[1]

| $KNO_3$ (g/l) | % Embryos with Shoots | Average Number of Shoots for Embryos with Shoots[2] | |
|---|---|---|---|
| | | $x \pm S.E.$ | Range |
| 0 | 0 | 0 | — |
| 1.9 | 25% | 4.8 ± 2.4 | 1–14 |
| 3.0 | 50% | 8.4 ± 2.6 | 1–24 |
| 6.9 | 60% | 15.1 ± 2.9 | 2–38 |
| 10.0 | 50% | 14.0 ± 3.5 | 1–32 |

[1]The results of both '2/3' and multiple horizontal cutting methods were combined; shoot induction medium contained: MS basal salts without $KNO_3$, modified Nitsch's Vitamins, 40 mg/l adenine sulfate, 3% sucrose with 0.5 mg/l BA and 0.1 mg/l NAA.
[2]x is the average number of shoots/shooting embryo; S.E. is standard error, N = 20.

TABLE 4

Effect of addition of modified Nitsch's Vitamin solution to shoot induction medium on the shooting response of four sunflower cultivars.[1]

| Cultivar | Medium[2] | % Cotyledons with shoots | Avg. No. of Shoot Shooting Cotyledons[3] | Range |
|---|---|---|---|---|
| 'Mammoth Russian' | + | 35% | 9.2 | 1-14 |
|  | − | 35% | 4.1 | 2-19 |
| Inbred 4M | + | 25% | 4.8 | 1-14 |
|  | − | 25% | 7.2 | 1-14 |
| Inbred 5F | + | 65% | 7.4 | 2-18 |
|  | − | 79% | 11.1 | 1-39 |
| Inbred 5MS[4] | + | 60% | 10.5 | 1-38 |
|  | − | 80% | 27.6 | 2-68 |

[1] The single horizontal cut method was employed throughout, mature seeds were employed except as noted for 5MS
[2] Shoot induction contained MS salts with 6.9 g/l KNO$_3$, 40 mg/l adenine sulfate, 3% sucrose with 0.5 mg/l BA and 0.1 mg/l NAA; (−) without modified Nitsch's vitamins; (+) with Nitsch's Vitamins.
[3] In this experiment (with N = 20), if the difference in average number of shoots/shooting cotyledons is greater than 6.3 then the difference is significant to the 5% level.
[4] Due to persistant microbial contamination of mature 5MS seeds, immature seeds were employed.

TABLE 5

Comparison of Vitamin solutions used in sunflower tissue culture.
Concentrations (mg/l).

| Components | Nitsch's | Modified Nitsch's[1] | MS[2] | G-T[3,4] | Paterson and Everett[5] | Sadhu[6] |
|---|---|---|---|---|---|---|
| nicotinic acid | 5.0 | 1.5 | 0.5 | 0.5 | 0.5 | 0.5 |
| thiamine HCL | 0.5 | 0.5 | 0.1 | 0.1 | 1.0 | 0.2 |
| pyridoxine HCL | 0.5 | 0.5 | 0.5 | 0.5 | 0.5 | 0.5 |
| myo-inositol | 100 | 100 | 100 | 500 | 100-500 | 100 |
| glycine | — | 2.0 | 2.0 | 3.0 | 2.0 | 2.0 |
| cysteine | — | — | — | 1.0 | — | — |
| Ca-panthothenate | — | — | — | 1.0 | — | — |
| adenine sulfate | — | — | — | 40 | 40 | — |
| biotin | 0.05 | 0.25 | — | — | — | — |
| folic acid | 0.5 | 0.5 | — | — | — | — |

[1] Nitsch and Nitsch (1967) Planta 72:355-370.
[2] Murashige and Skoog (1962) Physiol. Planta 15:473-497.
[3] Georgieva-Todorova et al. (1980) Ninth International conference on Sunflower, Torremolinas, Spain, Vol. 1, p. 122; and Bohorova et al. (1985) Z. Pflanzenzüchtg. 95:35-44.
[4] Casein hydrolysate (500 mg/l) was also included.
[5] Paterson and Everett (1985) Plant Science 42:125-132.
[6] Sadhu (1974) Indian J. Exp. Biol. 12:110-111.

TABLE 6

Shoot induction response of sunflower inbred line 5F to various levels of adenine sulfate and inositol.[1]

| | % Embryos with Shoots | Average Number of Shoots for Embryos with Shoots | |
|---|---|---|---|
| | | $x \pm SE^2$ | Range |
| Adenine Sulfate (mg/l) | | | |
| 0 | 38% | 15.0 ± 1.9 | 8-26 |
| 10 | 67% | 14.1 ± 3.4 | 3-54 |
| 40 | 48% | 28.5 ± 6.5 | 3-57 |
| 100 | 43% | 10.6 ± 3.0 | 1-29 |
| Myo-Inositol (mg/l)[3] | | | |
| 0 | 25% | 17.4 ± 9.4 | 3-54 |
| 100 | 55% | 14.3 ± 4.1 | 3-49 |
| 500 | 35% | 23.6 ± 7.2 | 5-56 |
| 1000 | 20% | 15.3 ± 5.9 | 5-29 |

[1] Explants were prepared by either the 2/3 cut or multiple horizontal cut method and the results were combined.
[2] x = Average number of shoots/shooting embryo and SE = standard error.

We claim:

1. A method for regenerating a sunflower plant by inducing shoots from an explant comprising cotyledon tissue of a non-germinated embryo which method comprises the steps of:

(a) preparing said explant by cutting said non-germinated embryo such that a cut surface of said explant comprises cotyledon tissue and such that substantially all of the induced shoots derive from single cotyledon cells of said explant and development of the axil of said embryo in said explant is disrupted;

(b) culturing said explant on a shoot-inducing, non-callus inducing medium which comprise a shoot-induction effective combination of an auxin selected from the group consisting of 1-naphthaleneacetic acid and indole-3-acetic acid and a cytokinin which is benzyl adenine, a basal mineral salts combination suitable for sunflower tissue growth containing KNO$_3$ and a carbohydrate such that said cut surface is placed in contact with said shoot-inducing medium, thereby inducing a shoot from cotyledon tissue of said explant;

(c) rooting said shoot induced from said explant thereby producing a plantlet; and (d) growing said plantlet in a plant growth medium thereby producing said sunflower plant and thereby regenerating said sunflower plant from said explant comprising cotyledon tissue.

2. The method of claim 1 wherein said explant is prepared using the single horizontal cut method which comprises making a horizontal cut across said non-germinated embryo, parallel to and above the line of cotyledon attachment, thereby producing an excised cotyledon explant, said horizontal cut being made such that substantially all of the embryo meristem is removed from said excised cotyledon explant.

3. The method of claim 2 wherein said horizontal cut is made at least about 0.5 mm above the line of cotyledon attachment of said embryo.

4. The method of claim 2 wherein said horizontal cut is made between about 0.5 to 1 mm above the line of cotyledon attachment of said embryo.

5. The method of claim 2 further comprising cutting said excised cotyledon explant into multiple segments such that the segments are of a size sufficient to support shoot induction.

6. The method of claim 5 wherein said excised cotyledon explant is cut into multiple segments with additional horizontal cuts.

7. The method of claim 5 wherein said cotyledon explant is cut into 3 or 4 segments of approximately the same size.

8. The method of claim 5 wherein said segments of said excised cotyledon explant are about 1 to 1.5 mm thick.

9. The method of claim 1 wherein said explant is prepared by the ⅝ cut method which comprises:

(a) excising most but not all of the cotyledon tissue from the axil of said embryo by making a horizontal cut across said embryo, parallel to and above the line of cotyledon attachment but not more than about 1 mm above the line of cotyledon attachment to produce an axil-containing explant;

(b) cutting said axil containing explant along a line extending from one side of the embryo radicle to the surface of said horizontal cut such that the embryo meristem is not split and said axil-containing explant is divided into two segments: a larger segment, about ⅝ the size of said axil-containing explant, and a smaller segment about ⅜ the size of said axil-containing explant.

10. The method of claim 9 wherein said horizontal cut is made above the line of cotyledon attachment such that any discernible primordial leaves at the tip of the meristem remain attached to the meristem.

11. The method of claim 9 wherein said horizontal cut is made from about 0.1 to 1 mm above the line of cotyledon attachment.

12. The method of claim 9 wherein said horizontal cut is made from about 0.1 to 0.3 mm above the line of cotyledon attachment.

13. The method of claim 9 wherein said axil-containing explant is cut vertically along a line extending from one side of the embryo radicle to the surface of said horizontal cut.

14. The method of claim 1 wherein said non-germinated embryo is a mature embryo.

15. The method of claim 1 wherein said non-germinated embryo is an immature embryo having full-formed cotyledons.

16. The method of claim 1 wherein said embryo is an embryo of a sunflower inbred line.

17. The method of claim 1 further comprising after said culturing step a shoot elongation step in which induced shoots that are too short for effective rooting are cultured on a shoot elongation medium until they are a length suitable for effective rooting.

18. The method of claim 1 wherein the concentration of $KNO_3$ is about 1.9 g/l to about 10 g/l, inclusive.

19. The method of claim 18 wherein said basal mineral salts combination comprises $KNO_3$ at a concentration of about 6.9 g/l to about 10 g/l, inclusive.

20. The method of claim 18 wherein said shoot induction medium further comprises adenine sulfate at a concentration of about 10 to about 100 mg/l, inclusive.

21. The method of claim 18 wherein said shoot induction medium further comprises myo-inositol at a concentration of about 100 to about 1000 mg/l, inclusive.

22. The method of claim 18 wherein said shoot induction medium further comprises vitamin solution suitable for sunflower tissue growth.

23. The method of claim 18 wherein said shoot induction medium further comprises gibberellic acid at a concentration of about 0.1 mg/l.

24. The method of claim 18 wherein said carbohydrate is selected from a group consisting of sucrose, glucose and a combination of sucrose and glucose.

25. The method of claim 18 wherein said shoot induction effective combination of an auxin and a cytokinin comprises benzyl adenine at a concentration from about 0.5 to about 2.0 mg/l, inclusive, and 1-naphthaleneacetic acid at a concentration from about 0.1 to about 1.0 mg/l, inclusive.

26. The method of claim 25 wherein said shoot induction effective combination of an auxin and a cytokinin comprises about 0.5 mg/l benzyl adenine and about 0.1 mg/l 1-naphthalene acetic acid.

27. The method of claim 26 wherein said shoot induction medium further comprises about 40 mg/l adenine sulfate.

28. The method of claim 26 wherein said shoot induction medium further comprises about 100 mg/l myo-inositol.

29. The method of claim 26 wherein said shoot induction medium further comprises a vitamin solution suitable for sunflower tissue growth.

30. The method of claim 26 wherein said shoot induction medium further comprises gibberellic acid at a concentration of about 0.1 mg/l.

31. The method of claim 26 wherein said basal mineral salts combination suitable for sunflower tissue growth is MS basal salts medium comprising about 6.9 g/l $KNO_3$ wherein said shoot induction medium further comprises about 40 mg/l adenine sulfate and about 100 mg/l myo-inositol, and wherein said carbohydrate is glucose.

32. The method of claim 31 wherein said shoot induction medium further comprises a vitamin solution effective for growth of sunflower tissue.

33. The method of claim 31 wherein said shoot induction medium further comprises about 0.1 mg/l gibberellic acid.

34. The method of claim 1 wherein said rooting step comprises (a) dipping said shoot-induced from said explant in a rooting solution which comprises either indole-3-acetic acid or indole-3-butyric acid, followed by
(b) culturing said shoot on MS medium.

35. The method of claim 18 wherein said rooting step comprises:
(a) dipping said shoot induced from said explant in a rooting solution which comprises either indole-3-acetic acid or indole-3-butyric acid, followed by
(b) culturing said shoot on MS medium.

36. The method of claim 1 wherein said auxin is 1-naphthaleneacetic acid.

* * * * *

UNITED STATES PATENT AND TRADEMARK OFFICE
CERTIFICATE OF CORRECTION

PATENT NO. : 5,030,572

DATED : July 9, 1991

INVENTOR(S) : Christopher J. Power and Ebrahim Firoozabady

It is certified that error appears in the above-identified patent and that said Letters Patent is hereby corrected as shown below:

Col. 1, line 33, "see" should read --See--.
column 2, line 37, please rewrite "017904" as --0170904--. At column 3, line 3, please rewrite "al., 1985" as --al. (1985)--. At column 3, line 24, please delete the comma after "et al.". At column 4, line 6, please rewrite "abacisic" as --abscisic--. At column 4, line 9, please rewrite "rotting" as --rooting--. At column 4, line 58, please rewrite "as" as --was--. At column 4, line 60, please rewrite "one" as --on--. At column 6, line 16, "expiants" should read --explants--. column 8, line 8, please insert a period after "features". At column 10, bridging lines 33-34, please rewrite "cotyldeon" as --cotyledon--. At column 12, line 16, please insert a period after "appeared". At column 12, line 29, please rewrite "KNO3" as --KNO$_3$--. At column 12, line 32, please rewrite "0:1" as --0.1--. At column 14, line 2, please insert --which-- after "from". At column 14, line 49, please insert a period after "employed". At column 15, line 16, please rewrite "nave" as --have--. At column 15, line 18, please rewrite "0:5" as --0.5--. At column 15, line 34, please rewrite "layo-inositol" as --myo-inositol--. At column 15, line 36, please rewrite "myo-inusitol" as --myo-inositol--. At column 15, line 37, please insert a period after "response". At column 17, line 45, please rewrite "co" as --to--. At column 18, line 56, please insert a period after "respectively". At column 19, line 15, please rewrite "co" as --to--. At column 21, line 16, please insert a comma between "5)" and "40". At column 21, line 17, please rewrite "0.1 mg/l shoot" as --0.1 mg/l NAA. At column 21, line 30, please insert a period after "appeared". At column 21, line 47, please rewrite "0:5" as --0.5--. At column 21, line 62, please rewrite "6:9" as --6.9--.

UNITED STATES PATENT AND TRADEMARK OFFICE
CERTIFICATE OF CORRECTION

PATENT NO. : 5,030,572

DATED : July 9, 1991

INVENTOR(S) : Christopher J. Power and Ebrahim Firoozabady

It is certified that error appears in the above-identified patent and that said Letters Patent is hereby corrected as shown below:

At column 21, line 62, please delete the semi-colon after "Nitsch's". At column 21, bridging lines 66-67, please insert a comma after "elongated". At column 22, circa line 22, please rewrite "0:3" as --0.3--. At column 22, circa line 39, please insert a comma after "myo-inositol". At column 22, line 54, please insert a comma after "myo-inositol". At column 22, line 66, please rewrite "FI" as --F1--. At column 22, last line, please rewrite "FI" as --F1--. At column 23, line 3, please rewrite "FI" as --F1--. At column 24, Table 1, first column, line 15 of the Table (under the heading "Component"), please rewrite "CoCl$_2$6H$_2$O" as --CaCl$_2$6H$_2$O--. At column 25, Table 6, first column, line 6 of the Table, please delete superscript "3".

IN THE CLAIMS

At claim 1, line 13, please rewrite "comprise" as --comprises--. At claim 22, line 2, please insert --a-- after "comprises".

Signed and Sealed this

First Day of June, 1993

Attest:

*Attesting Officer*

MICHAEL K. KIRK

*Acting Commissioner of Patents and Trademarks*